United States Patent [19]

Taskis

[11] 4,272,542
[45] Jun. 9, 1981

[54] USE OF DI-SODIUM AND DI-POTASSIUM SALTS OF DICARBOXYLIC AMINO ACIDS AND TRI- OR DI-SODIUM OR POTASSIUM PHOSPHATE TARTRATE OR CITRATE TO IMPROVE THE TASTE OF IN VIVO HYDROLYSABLE ESTERS OF α-AMINO PENICILLINS AND CEPHALOSPORINS

[75] Inventor: Charles B. Taskis, Worthing, England

[73] Assignee: Beecham Group Limited, England

[21] Appl. No.: 709,123

[22] Filed: Jul. 27, 1976

[30] Foreign Application Priority Data

Aug. 7, 1975 [GB] United Kingdom ............... 32976/75

[51] Int. Cl.³ ..................... A61K 31/43; A61K 31/66; A61K 31/195
[52] U.S. Cl. ................................. 424/271; 424/119; 424/224; 424/319
[58] Field of Search ................ 424/119, 271, 224, 319

[56] References Cited

U.S. PATENT DOCUMENTS

| | | | |
|---|---|---|---|
| 3,317,389 | 5/1967 | Granatek et al. | 424/114 |
| 3,549,746 | 12/1970 | Granatek et al. | 424/271 |
| 3,626,056 | 12/1971 | Granatek et al. | 424/271 |
| 3,697,507 | 10/1972 | Frederiksen et al. | 424/271 |
| 3,939,270 | 2/1976 | Ekstrom et al. | 424/271 |
| 3,997,662 | 12/1976 | Pinnert et al. | 424/119 |

Primary Examiner—Douglas W. Robinson
Attorney, Agent, or Firm—Jacobs & Jacobs

[57] ABSTRACT

In-vivo hydrolysable esters of certain α-amino penicillins and cephalosporins have been rendered relatively tasteless by formulating into reconstitutable powders with a disodium or dipotassium salt of a di-carboxylic amino acid or tri- or di-sodium or -potassium phosphate, tartrate or citrate.

15 Claims, No Drawings

USE OF DI-SODIUM AND DI-POTASSIUM SALTS OF DICARBOXYLIC AMINO ACIDS AND TRI- OR DI-SODIUM OR POTASSIUM PHOSPHATE TARTRATE OR CITRATE TO IMPROVE THE TASTE OF IN VIVO HYDROLYSABLE ESTERS OF α-AMINO PENICILLINS AND CEPHALOSPORINS

The present invention relates to powders which may be reconstituted to form orally administrable solutions or suspensions of basic medicaments and to certain components thereof.

A common method of administering medicaments is in a solution or suspension which has been reconstituted from a powder by the addition of water. For example, penicillins are often provided in admixture with excipients such as sugar, colours, preservatives, anti-foams, flavours and the like in the form of a reconstitutable powder. One disadvantage with known formulations of this kind is that they frequently allow the taste of the medicament to be detected and in the case of an unpleasant tasting medicament it can cause children to object to taking the medicament.

Belgian Pat. No. 826379 describes a powder which may be reconstituted into an orally administrable pharmaceutical composition by the addition of water which powder contains (a) fine particles of a water-soluble acid addition salt of an in-vivo hydrolysable ester of a penicillin or cephalosporin which has an amino group in the acylamino side chain and which fine particles are substantially or wholly coated by a water insoluble coating agent, (b) a water-soluble salt of a weak organic acid and (c) conventional excipients.

The method of preparing such medicaments is often expensive and laborious, especially in the case of spray-drying a preferred method due to the quality of the finished product.

We have now discovered that an improvement and modification of the above powders may be made by not including a coating agent in the powder. Such powders are relatively inexpensive and simple to prepare.

Accordingly the present invention provides a powder which may be reconstituted into an orally administrable pharmaceutical composition in suspension or solution form by the addition of water which powder contains (a) fine particles of a compound of the formula (I) or (II):

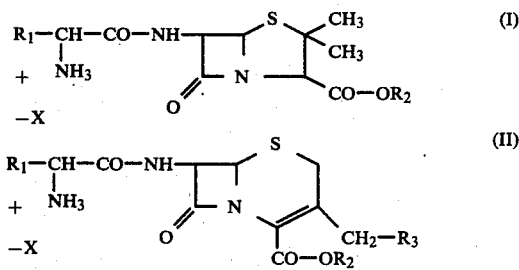

wherein $R_1$ is a phenyl, 4-hydroxyphenyl or cyclohexadienyl group; $R_2$ is a group such that the group $CO_2R_2$ is readily hydrolysed in-vivo to a $CO_2H$ group or salt thereof; $R_3$ is a hydrogen atom or an acetoxyl group; and $X^-$ is a pharmaceutically acceptable anion; and (b) a disodium or dipotassium salt of a di-carboxylic amino acid or tri- or di-sodium or potassium phosphate, tartrate or citrate; the weight ratio of the compound of the formula (I) or (II) to the disodium or dipotassium salt of a di-carboxylic amino acid or tri- or di-sodium or potassium phosphate, tartrate or citrate being from 2:1 to 1:5.

By 'fine particles' are meant particles in the size range $5\mu$–$500\mu$ or aggregates of such particles, preferably in the range of $10\mu$–$300\mu$.

Most suitably the powders of this invention contain a compound of the formula (I) or (II) wherein $R_2$ is an acetoxymethyl, pivaloyloxymethyl or phthalidyl group.

Most suitably the powders of this invention contain a compound of the formula (I) wherein $R_1$ is a phenyl group.

Most suitably the acid used to salt the amino group of the acylamino side chain is hydrochloric acid.

A preferred medicament for inclusion in the powders of this invention is ampicillin phthalidyl ester hydrochloride.

Another preferred medicament for inclusion in the powders of this invention is amoxycillin phthalidyl ester hydrochloride. Suitably the salts for use in this invention are sodium salts.

Preferred salts for use in this invention include di- and tri-sodium citrate. Tri-sodium citrate is a particularly useful salt for inclusion in the powders of this invention.

The compounds of this invention often contain di- or tri-sodium citrate and a compound of the formula (I) or (II) in the ratio of 2:1 to 1:2 by weight.

Suitably the ratio of tri-sodium citrate to the compound of the formula (I) is between 2:1 and 1:1 by weight.

A preferred composition of this invention contains tri-sodium citrate and ampicillin phthalidyl ester hydrochloride in the ratio of 2:1 by weight.

The compositions of this invention may also contain conventional pharmaceutical excipients. Suitable excipients for use in this invention include conventional flavouring oils, saccharin salts, waxes and the like in conventional quantities. Such excipients will be well known to those skilled in formulating penicillins or cephalosporins.

The compositions of this invention may be prepared by methods such as blending or mixing conventionally used in the preparation of reconstitutable pharmaceutical compositions, such as those containing penicillins or cephalosporins.

Suitable methods of mixing include 'dry mix' or mixing in a 'Y-cone blender'.

The following Examples are illustrative of the invention:

EXAMPLE 1

A reconstitutable powder was prepared from:

| | |
|---|---|
| Ampicillin phthalidyl ester hydrochloride | 1.72 g |
| Anhydrous trisodium citrate | 3.44 g |
| Preservatives | 0.1 g |
| Flavours | 1.2 g |
| Colours | 0.003 g |
| Caster Sugar | to 40 g |

The preservatives, anhydrous trisodium citrate, colour and flavourings were mixed with a proportion of the sugar and milled. This material was then blended with the remainder of the sugar and milled ampicillin phthalidyl ester hydrochloride in a suitable mixer such as a 'Y-cone', 'Oblacone' or 'Rotocube'.

'Y-cone', 'Oblacone' and 'Rotocube' are Registered Trade Marks.

EXAMPLE 2

Using the method of Example 1 the following reconstitutable powder was prepared:

| | |
|---|---|
| Ampicillin phthalidyl ester hydrochloride | 2.49 g |
| Anhydrous trisodium citrate | 2.49 g |
| Conventional additives | 6.29 g |
| Caster sugar | up to 45.00 g |

What we claim is:

1. A powder which may be reconstituted into an oral pharmaceutical composition in suspension or solution form by the addition of water which powder comprises
   (a) fine particles of a penicillin of the formula

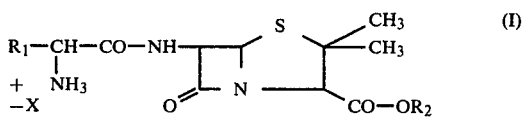

wherein
$R_1$ is phenyl, 4-hydroxyphenyl or cyclohexadienyl;
$R_2$ is acetoxymethyl, pivaloyloxymethyl or phthalidyl;
and
$X^-$ is a pharmaceutically acceptable anion; and
(b) a di-sodium or di-potassium salt of a di-carboxylic amino acid or tri- or di-sodium or potassium phosphate, tartrate or citrate; the weight ratio of said penicillin to said di-sodium or di-potassium salt of a di-carboxylic amino acid or tri- or di-sodium or potassium phosphate, tartrate or citrate being from 2:1 to 1:5.

2. A powder according to claim 1 wherein the penicillin is ampicillin phthalidyl ester hydrochloride or amoxycillin phthalidyl ester hydrochloride.

3. A powder according to claim 1 wherein component (b) is di- or tri-sodium citrate.

4. A powder which may be reconstituted into an orally administrable pharmaceutical composition in suspension or solution form by the addition of water which powder comprises (a) ampicillin phthalidyl ester hydrochloride and (b) tri-sodium citrate, in the weight ratio of 1:2.

5. A powder according to claim 1 wherein said fine particles have a size range of $5\mu$ to $500\mu$ or are aggregates of particles having said size range.

6. A powder according to claim 1 wherein said fine particles have a size range of $10\mu$ to $300\mu$ or are aggregates of particles having said size range.

7. A powder according to claim 1 wherein $R_1$ is phenyl.

8. A powder according to claim 1 wherein said penicillin is in the form the hydrochloride salt.

9. A powder according to claim 1 wherein said penicillin is ampicillin phthalidyl ester hydrochloride.

10. A powder according to claim 1 wherein said penicillin is amoxycillin phthalidyl ester hydrochloride.

11. A powder according to claim 1 wherein component (b) is tri-sodium citrate.

12. A powder according to claim 1 wherein component (b) is di- or tri-sodium citrate and the ratio of penicillin to said di- or tri-sodium citrate is from 2:1 to 1:2.

13. A powder according to claim 1 wherein component (b) is tri-sodium citrate and the weight ratio is 2:1 to 1:1.

14. A powder according to claim 1 which additionally contains a conventional pharmaceutical excipient or a mixture of excipients.

15. A powder which may be reconstituted into an oral pharmaceutical composition in suspension or solution form by the addition of water, which powder comprises (a) ampicillin phthalidyl ester hydrochloride and (b) tri-sodium citrate, in the weight ratio of 1:1.

* * * * *